United States Patent [19]

Carnahan

[11] 4,273,717
[45] Jun. 16, 1981

[54] MONOCAPPED BISPHENOL SALTS AND METHOD OF MAKING

[75] Inventor: James C. Carnahan, Schenectady, N.Y.

[73] Assignee: General Electric Company, Schenectady, N.Y.

[21] Appl. No.: 104,424

[22] Filed: Dec. 17, 1979

Related U.S. Application Data

[62] Division of Ser. No. 942,957, Sep. 18, 1978, abandoned.

[51] Int. Cl.³ ........................................... C07D 309/22
[52] U.S. Cl. ............................................. 260/345.9 R
[58] Field of Search ................................. 260/345.9 R

[56] References Cited

FOREIGN PATENT DOCUMENTS 473714  10/1975  U.S.S.R. ............................ 260/345.9 R

OTHER PUBLICATIONS

Comp. Rend, Feb. 1, 1965, (Index Chemicus) 17(6) 6/7/65.
Index Chemicus 21(3) 4/25/66.

*Primary Examiner*—Paul J. Killos
*Attorney, Agent, or Firm*—William A. Teoli; James C. Davis, Jr.

[57] ABSTRACT

Monocapped bisphenol salts are provided including the monocapped salt of 2,2-bis(4-hydroxyphenyl)propane. Capping is effected by contacting a bisphenol and dihydropyran in the presence of an anhydrous organic solvent and a condensation catalyst. Subsequent decapping is readily achieved under acid conditions. The monocapped bisphenol salts are useful for making intermediate bisphenol oligomers.

5 Claims, No Drawings

MONOCAPPED BISPHENOL SALTS AND METHOD OF MAKING

This is a division of application Ser. No. 942,957, (abandoned), filed Sept. 18, 1978.

BACKGROUND OF THE INVENTION

The present invention relates to monocapped bisphenol salts which can be used to make bisphenol dimers, such as bisphenol formal dimers. More particularly, the present invention relates to the use of dihydropyran as a capping agent for bisphenols and the separation of the monocapped bisphenol as a phenoxide salt from the dicapped material.

Prior to the present invention, dihydropyran was used with monophenols as a protective group, McOmie, Protective Groups In Organic Chemistry, Plenum Press, New York, 1973. It has also been found that dihydropyran can be used as a capping agent for bisphenols which are dissolved in an anhydrous ether and utilized with a condensation agent, such as toluene sulfonic acid. It would be desirable to be able to make monocapped bisphenols in the presence of bicapped bisphenols and readily separate these dihydropyran bisphenol reaction products from each other.

The present invention is based on the discovery that monocapped bisphenol salts of the formula

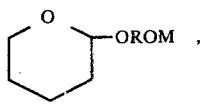    (1)

can be made by effecting reaction between 0.5 to 1.0 moles of dihydropyran per mole of a bisphenol of the formula,

H—O—R—O—H    (2)

in the presence of an organic solvent and a condensation catalyst, and thereafter forming the monocapped bisphenol salts of formula (1) by adding an alkali metal base to the reaction mixture to effect the precipitation of the monocapped bisphenol salt from the mixture.

There is provided by the present invention, a method for making a monocapped bisphenoxide salt of formula (1) which comprises (1) effecting contact at temperatures of from 0° C. to 100° C. under substantially anhydrous conditions between a bisphenol of formula (2), and from about 0.5 to about 1 mole of dihydropyran per mole of the bisphenol in the presence of a condensation catalyst and an organic solvent, (2) stirring a mixture comprising the resulting bisphenol condensation product of (1) and more than 1 equivalent of alkali metal or alkali metal ion per equivalent of nuclear bound hydroxy radical of the bisphenol condensation product and (3) recovering the resulting phenoxide salt as a solid from the mixture of (2), where R is a $C_{(6-30)}$ divalent organic radical and M is an alkali metal ion.

The divalent aromatic organic radicals included by R of formulas (1) and (2) are $C_{(6-13)}$ divalent aromatic hydrocarbon radicals and halogenated derivatives thereof, and divalent organic radicals of the formula, $$-R^1-Q-R^1-,$$

where $R^1$ is selected from divalent $C_{(6-13)}$ aromatic hydrocarbon radicals and halogenated derivatives thereof and Q is selected from —O—, —S—, —Si—,

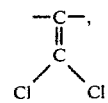

fluorenyl, cyclohexyl, and $-C_yH_{2y}-$, where y is an integer having a value of from 1–5 inclusive.

There are included within the bisphenols of formula (2)

2,2-bis-(2-hydroxyphenyl)propane;
2,4'-dihydroxydiphenylmethane;
bis-(2-hydroxyphenyl)-methane;
2,2-bis-(4-hydroxyphenyl)-propane, hereinafter identified as "bisphenol-A" or "BPA";
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
4,4'-dihydroxy-3,3',5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfide; etc.

Alkali metal bases which can be used to form the alkali metal salts of formula (1) are, for example, alkali metal hydroxides, such as sodium hydroxide, potassium hydroxide, lithium hydroxide, etc.; alkali metal such as sodium, potassium, lithium, etc.; ammonium hydroxide, rubidium hydroxide, cesium, hydroxide, etc. Condensation catalysts which can be employed to produce the bisphenol dihydropyran reaction products are, for example, toluene sulfonic acid, methane sulfonic acid, acidic ion exchange resins, anhydrous HCl, HBr or $H_2SO_4$. In addition to diethylether, there also can be used as organic solvents tetrahydrofuran, dioxan, 1,2-dimethoxyethane, acetonitrile.

In the practice of the invention the monocapped bisphenol salt of formula (1) can be made by initially forming a dihydropyran reaction product of the bisphenol by effecting contact between the bisphenol and the dihydropyran in the presence of a condensation catalyst and an organic solvent. It has been found that the initial condensation reaction is exothermic and the mixture can be refluxed for an additional 0.5 to 1 hour or more after the addition has been completed. Experience has shown that the dicapped bisphenol product formed during the condensation step can be recycled to produce additional monocapped product by heating the dicapped material in the presence of additional bisphenol and condensation catalyst to effect a redistribution.

In the practice of the invention, the monocapped bisphenol salt can be made by effecting reaction between dihydropyran and a bisphenol within the scope of formula (2) in the presence of a condensation catalyst and an organic solvent. The order of addition of the various reactants is not critical and the condensation reaction is preferably achieved under reflux conditions, although a temperature of between 0° C. to 100° C. can be employed.

The addition of the alkali metal base can be achieved by adding the base to the condensation reaction mixture while it is being agitated which will result in the formation of the monocapped bisphenol salt as a precipitate. The addition of the alkali metal base can be continued until no further precipitation occurs. Recovery of the monocapped bisphenol salt can be achieved in accordance with standard filtration techniques facilitated by washing of the precipitate with additional organic solvent, followed by drying. It has been found that the monocapped bisphenol salt is often recovered in the form of a hydrate such as trihydrate.

The monocapped bisphenol salts of the present invention can be used as intermediates for making bisphenol dimers as shown in my copending application RD-10328, filed concurrently herewith and assigned to the same assignee as the present invention.

In order that those skilled in the art will be better able to practice the invention, the following examples are given by way of illustration and not by way of limitation. All parts are by weight.

EXAMPLE 1

There was added 0.3 part of toluene sulfonic acid to a solution of 57 parts of bisphenol-A and about 300 parts of anhydrous diethylether. After the addition of the condensation catalyst was completed, there was added 21 parts of dihydropyran over a 3 minute period in the form of a 50% solution in diethylether. The reaction was found to be exothermic during the addition and the mixture was refluxed for an additional hour. Analysis of a titer of the mixture with a gel with permeation chromatograph showed that the condensation was complete.

There was then added a 25% aqueous solution of sodium hydroxide to the above condensation reaction mixture resulting in the formation of a precipitate. During the addition, the mixture was rapidly stirred. The addition of the sodium hydroxide solution was continued until no further precipitation occurred. The diethylether was then decanted from the mixture and the resulting precipitate was slurried with hot diethylether 3 times and then filtered. The solid filler cake was then washed with additional diethylether and allowed to dry. There was obtained 40.7 parts of the monocapped salt of bisphenol-A having the formula.

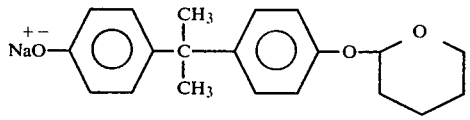

The identity of the above monocapped bisphenol salt hydrate was established by its C-13, proton NMR and its IR spectra.

A suspension of 5 parts of the above monocapped bisphenol salt in 40 parts of water was then treated with carbon dioxide by bubbling the carbon dioxide into the suspension. The resulting mixture was then extracted with ether resulting in the recovery of monocapped bisphenol-A.

A mixture of 66.8 parts of the monocapped bisphenol-A salt, 1 part of sodium hydroxide, and 240 parts of N-methylpyrrolidone was heated to 35° C. until most of the solid had dissolved. There was then added 212 parts of methylene chloride to the mixture which was then heated at 50° C. for 1 hour. The mixture was then allowed to cool and 50 parts of water was added and the mixture was then acidified with acetic acid, the total mixture amounting to about 500 parts. There was then added to the resulting mixture, about 100 parts of 6-N hydrochloric acid. The mixture was stirred at 37° C. for 1½ hours. After hydrolysis was completed, as shown by GPC, the product was isolated by extracting it from the mixture with diethylether and thereafter washing the ethereal solution with water, followed by neutralizing it with sodium bicarbonate. Upon removal of the solvent, an oil was obtained which was dissolved in chloroform and triturated with hexane. There was obtained an 89% yield or 36 parts of a white crystalline product having a melting point of 130°-131.5° C. Based on method of preparation, the product was a bisphenol-A formal dimer having the formula,

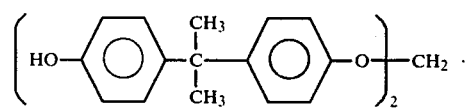

The identity of the dimer was further confirmed by its NMR, IR and mass spectra.

EXAMPLE 2

There was added 0.3 part of toluene sulfonic acid to a solution of 70 parts of 2,2(4-hydroxyphenyl)1,1-dichloroethylene and about 500 parts of anhydrous diethylether. After the addition of the condensation catalyst was completed, there was added 21 parts of dihydropyran over a 3 minute period in the form of a 50% solution in diethylether. The reaction was found to be exothermic during the addition and the mixture was refluxed for an additional hour. Analysis of a titer of the mixture with a gel permeation chromatograph showed that the condensation was complete.

There was added a 25% aqueous solution of sodium hydroxide to the above condensation reaction mixture resulting in the formation of a precipitate. During the addition, the mixture was rapidly stirred. The addition of the sodium hydroxide solution was continued until no further precipitation occurred. The diethylether was then decanted from the mixture and the resulting precipitate was slurried with hot diethylether 3 times and then filtered. The solid filler cake was then washed with additional diethylether and allowed to dry. There was obtained 43.4 parts of the monocapped salt of 2,2(4-hydroxyphenyl)-1,1-dichloroethylene.

Although the above examples are directed to only a few of the very many variables of the present invention, it should be understood that there is a much broader class of monocapped bisphenol salts as shown by formula (1) which can be made by effecting condensation between a bisphenol within formula (2) and dihydropyran in the presence of a condensation catalyst, followed by the precipitation of a monocapped bisphenol salt from the resulting condensation mixture by the addition of an alkali metal or alkali metal hydroxide to the condensation mixture. These monocapped bisphenol salts can be used to make the corresponding bisphenol formal dimers or can be used as chain terminators for a variety of organic polymers such as polycarbonates, polyesters, polyformals, etc.

What I claim as new and desire to secure by Letters Patent of the United State is:

1. Monocapped bisphenol salts of the formula,

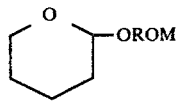

where R is a $C_{(6-30)}$ divalent organic radical selected from the class consisting of $C_{(6-13)}$ divalent aromatic hydrocarbon radicals and halogenated derivatives thereof and divalent organic radicals of the formula, $$-R^1-Q-R^1-,$$

where $R^1$ is selected from divalent $C_{(6-13)}$ aromatic hydrocarbon radicals and halogenated derivatives thereof and Q is selected from —O—, —S—, —Si—,

fluorenyl, cyclohexyl, and —$C_yH_{2y}$—, where y is an integer having a value of from 1–5 inclusive.

2. A monocapped bisphenol salt of claim 1, where R is

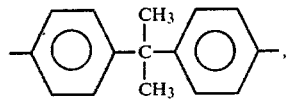

and M is $Na^+$.

3. A monocapped bisphenol salt of claim 1, where R is

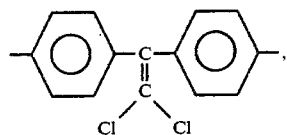

and M is $Na^+$.

4. The compound

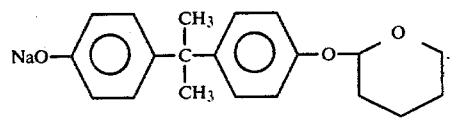

5. The compound

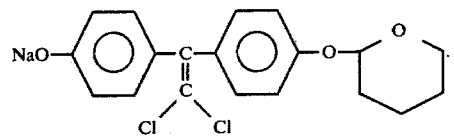

* * * * *